(12) United States Patent
Hill et al.

(10) Patent No.: US 9,050,106 B2
(45) Date of Patent: Jun. 9, 2015

(54) OFF-WALL ELECTRODE DEVICE AND METHODS FOR NERVE MODULATION

(71) Applicant: BOSTON SCIENTIFIC SCIMED, INC., Maple Grove, MN (US)

(72) Inventors: Jason P. Hill, Brooklyn Park, MN (US); Mark L. Jenson, Greenfield, MN (US)

( * ) Notice: Subject to any disclaimer, the term of this patent is extended or adjusted under 35 U.S.C. 154(b) by 245 days.

(21) Appl. No.: 13/725,785

(22) Filed: Dec. 21, 2012

(65) Prior Publication Data

US 2013/0172881 A1 Jul. 4, 2013

Related U.S. Application Data

(60) Provisional application No. 61/581,430, filed on Dec. 29, 2011.

(51) Int. Cl.
*A61B 18/14* (2006.01)
*A61B 18/00* (2006.01)

(52) U.S. Cl.
CPC ... *A61B 18/1492* (2013.01); *A61B 2018/00404* (2013.01); *A61B 2018/00434* (2013.01); *A61B 2018/00511* (2013.01); *A61B 2018/00267* (2013.01); *A61B 2018/00577* (2013.01); *A61B 2018/1435* (2013.01)

(58) Field of Classification Search
USPC ...................................................... 607/2, 42
See application file for complete search history.

(56) References Cited

U.S. PATENT DOCUMENTS

| | | | |
|---|---|---|---|
| 164,184 A | 6/1875 | Kiddee | |
| 1,167,014 A | 1/1916 | O'Brien | |
| 2,505,358 A | 4/1950 | Gusberg et al. | |
| 2,701,559 A | 2/1955 | Cooper | |
| 3,108,593 A | 10/1963 | Glassman | |
| 3,108,594 A | 10/1963 | Glassman | |
| 3,540,431 A | 11/1970 | Mobin | |
| 3,952,747 A | 4/1976 | Kimmell | |

(Continued)

FOREIGN PATENT DOCUMENTS

| | | |
|---|---|---|
| DE | 10038737 A1 | 2/2002 |
| EP | 1053720 A1 | 11/2000 |

(Continued)

OTHER PUBLICATIONS

Van Den Berg, "Light echoes image the human body," OLE, Oct. 2001, p. 35-37.

(Continued)

*Primary Examiner* — Carl H Layno
*Assistant Examiner* — Jon Eric C Morales
(74) *Attorney, Agent, or Firm* — Seager, Tufte & Wickhem, LLC

(57) ABSTRACT

Medical devices and methods for making and using the same are disclosed. An example medical device may include an ablative catheter for nerve modulation through a wall of a blood vessel. The catheter may include a catheter sheath having a proximal end, a distal end, and a lumen extending from the proximal to the distal end. An elongate member may extend along a central elongate axis within the lumen of the catheter sheath. The elongate member having a proximal end and a distal end. An expandable ablative member may be coupled to the distal end of the elongate member having an insulative section connected to a bare electrode section. The ablative member may be configured to switch between a collapsed position and an expanded position.

18 Claims, 8 Drawing Sheets

(56) References Cited

U.S. PATENT DOCUMENTS

| | | |
|---|---|---|
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | LaFontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |

(56) References Cited

U.S. PATENT DOCUMENTS

| | | |
|---|---|---|
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |

(56) References Cited

U.S. PATENT DOCUMENTS

| | | |
|---|---|---|
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |

(56) References Cited

U.S. PATENT DOCUMENTS

| | | |
|---|---|---|
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |

(56) References Cited

U.S. PATENT DOCUMENTS

| | | |
|---|---|---|
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |

(56) References Cited

U.S. PATENT DOCUMENTS

| | | |
|---|---|---|
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |

(56) References Cited

U.S. PATENT DOCUMENTS

| | | |
|---|---|---|
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |

(56) References Cited

U.S. PATENT DOCUMENTS

| | | |
|---|---|---|
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0288730 A1 * | 12/2005 | Deem et al. ............ 607/42 |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |

(56) References Cited

U.S. PATENT DOCUMENTS

| | | |
|---|---|---|
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |

(56) References Cited

U.S. PATENT DOCUMENTS

| | | |
|---|---|---|
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

"IntraLuminal: Products," IntraLuminal Therapeutics, Inc., 2003, p. 1-9.

"Laser Catheter to Aid Coronary Surgery," TechTalk: MIT, Jan. 9, 1991, p. 1-4.

"Optical Coherence Tomography: Advantages of OCT," LightLab Imaging Technology.

"Optical Coherence Tomography: Image Gallery Cardiovascular Procedures," LightLab Imaging Technology.

"Optical Coherence Tomography: LightLab Imaging Starts US Cardiology Clinical Investigations," LightLab Imaging Technology, 2002.

"Optical Coherence Tomography: LightLab Sees Bright Prospects for Cardiac Application of OCT Technology," LightLab Imaging Technology, 2001, vol. 27, No. 35.

"Optical Coherence Tomography: What is OCT?," LightLab Imaging Technology.

"Optical Coherence Tomography: Why Use OCT?," LightLab Imaging Technology.

"Products—Functional Measurement," Volcano Functional Measurement Products US, Mar. 24, 2003, p. 1-2.

Brown et al., "Radiofrequency capacitive heaters: the effect of coupling medium resistivity on power absorption along a mouse leg," Physics in Medicine and Biology, 1993, p. 1-12, vol. 38.

Carrington, "Future of CVI: It's all about plaque: Identification of vulnerable lesions, not 'rusty pipes,' could become cornerstone of preventive cardiology," Diagnostic Imaging, 2001, p. 1-8.

Chen et al., "Percutaneous pulmonary artery denervation completely abolishes experimental pulmonary arterial hypertension in vivo," EuroIntervention, 2013, p. 1-8.

(56) References Cited

OTHER PUBLICATIONS

Cimino, "Preventing plaque attack," Mass High Tech, 2001, p. 1-2.

Dahm et al., "Relation of Degree of Laser Debulking of In-Stent Restenosis as a Predictor of Restenosis Rate," The American Journal of Cardiology, 2002, p. 68-70, vol. 90.

De Korte et al., "Characterization of Plaque Components With Intravascular Ultrasound Elastography in Human Femoral and Coronary Arteries In Vitro," Circulation, Aug. 8, 2000, p. 617-623.

Durney et al., "Radiofrequency Radiation Dosimetry Handbook," Oct. 1986, p. 1-2, Fourth Edition.

Durney et al., "Radiofrequency Radiation Dosimetry Handbook: Contents," Oct. 1986, p. 1-5, Fourth Edition.

Fournier-Desseux et al., "Assessment of 1-lead and 2-lead electrode patterns in electrical impedance endotomography," Physiological Measurement, 2005, p. 337-349. Vo. 26, Institute of Physics Publishing.

Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.

Fram et al., "Low Pressure Radiofrequency Balloon Angioplasty: Evaluation in Porcine Peripheral Arteries," JACC, 1993, p. 1512-1521, vol. 21, No. 6, American College of Cardiology.

Fujimori et al., "Significant Prevention of In-Stent Restenosis by Evans Blue in Patients with Acute Myocardial Infarction," American Heart Association, 2002.

Fujita et al., "Sarpogrelate, An Antagonist of 5-HT(2A) Receptor, Treatment Reduces Restenosis After Coronary Stenting," American Heart Association, 2002.

Gabriel, "Appendix A: Experimental Data," 1999, p. 1-21.

Gabriel, "Appendix C: Modeling the frequency dependence of the dielectric properties to a 4 dispersions spectrum," p. 1-6.

Gregory et al., "Liquid Core Light Guide for Laser Angioplasty," The Journal of Quantum Electronics, Dec. 1990, p. 2289-2296, vol. 26, No. 12.

Kaplan et al., "Healing after Arterial Dilatation with Radiofrequency Thermal and Nonthermal Balloon Angioplasty Sytems," Journal of Investigative Surgery, 1993, p. 33-52, vol. 6.

Kolata, "New Studies Question Value of Opening Arteries," The New York Times, Mar. 21, 2004, p. 1-5.

Konings et al., "Development of an Intravascular Impedance Catheter for Detection of Fatty Lesions in Arteries," IEEE Transactions on Medical Imaging, Aug. 1997, p. 439-446, vol. 16, No. 4.

Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.

Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.

Lima et al., "Efficacy and Safety of Oral Sirolimus to Treat and Prevent In-Stent Restenosis: A Pilot Study Results," American Heart Association, 2002, p. 2929.

Lima et al., "Systemic Immunosuppression Inhibits In-Stent Coronary Intimal Proliferation in Renal Transplant Patients," American Heart Association, 2002, p. 2928.

Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.

Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.

Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.

Popma et al., "Percutaneous Coronary and Valvular Intervention," p. 1364-1405.

Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.

Romer et al., "Histopathology of Human Coronary Atherosclerosis by Quantifying Its Chemical Composition With Raman Spectroscopy," Circulation, 1998, p. 878-885, vol. 97.

Schauerte et al., "Catheter Ablation of Cardiac Autonomic Nerves for Prevention of Vagal Atrial Fibrillation," Circulation, 2000, p. 2774-2780, vol. 102.

Scheller et al., "Intracoronary Paclitaxel Added to Contrast Media Inhibits In-Stent Restenosis of Porcine Coronary Arteries," American Heart Association, 2002, p. 2227.

Scheller et al., "Potential solutions to the current problem: coated balloon," EuroIntervention, 2008, p. C63-C66, vol. 4 (Supplement C).

Shaffer, "Scientific basis of laser energy," Clinics in Sports Medicine, 2002, p. 585-598, vol. 21.

Shmatukha et al., "MRI temperature mapping during thermal balloon angioplasty," Physics in Medicine and Biology, 2006, p. N163-N171, vol. 51.

Slager et al., "Vaporization of Atherosclerotic Plaques by Spark Erosion," J Am Coll Cardiol, 1985, p. 21-25.

Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.

Suselbeck et al., "In vivo intravascular electric impedance spectroscopy using a new catheter with integrated microelectrodes," Basic Res Cardiol, 2005, p. 28-34, vol. 100.

Suselbeck et al., "Intravascular electric impedance spectroscopy of atherosclerotic lesions using a new impedance catheter system," Basic Res Cardiol, 2005, p. 446-452, vol. 100.

Tepe et al., "Local Delivery of Paclitaxel to Inhibit Restenosis during Angioplasty of the Leg," The New England Journal of Medicine, 2008, p. 689-699, vol. 358.

US 8,398,630, 3/2013, Demarais et al., (withdrawn).

CardioVascular Technologies Inc., "Heated Balloon Device Technology," 11 pages, 2008.

Strategic Business Development, Inc., "Thermal and Disruptive Angioplasty: A Physician's Guide," 8 pages, 1990.

Zhang et al., "Non-contact Radio-Frequency Ablation for Obtaining Deeper Lesions," IEEE Transaction on Biomedical Engineering, vol. 50, No. 2, 6 pages, Feb. 2003.

Lazebnik et al., "Tissue Strain Analytics Virtual Touch Tissue Imaging and Qualification," Siemens Whitepaper, Oct. 2008, 7 pages.

Han et al., "Third-Generation Cryosurgery for Primary and Recurrent Prostate Caner," BJU International, vol. 93, pp. 14-18.

Zhou et al., "Mechanism Research of Ciyoanalgesia," Forefront Publishing Group, 1995.

Florete, "Cryoblative Procedure for Back Pain," Jacksonville Medicine, Oct. 1998, 10 pages.

Stevenson, "Irrigated RF Ablation: Power Titration and Fluid Management for Optimal Safety Efficacy," 2005, 4 pages.

Giliatt et al., "The Cause of Nerve Damage in Acute Compression," Trans Am Neurol Assoc, 1974: 99; 71-4.

Omura et al., "A Mild Acute Compression Induces Neurapraxia in Rat Sciatic Nerve," The International Journal of Neuroscience, vol. 114 (12), pp. 1561-1572.

Baun, "Interaction with Soft Tissue," Principles of General & Vascular Sonography, Chapter 2, pp. 23-24, Before Mar. 2012.

Blue Cross Blue Shield Medicaly Policy, "Surgery Section—MRI-Guided Focused Ultrasound (MRgFUS) for the Treatment of Uterine Fibroids and Other Tumors," 2005, 5 pages.

Gentry et al., "Combines 3D Intracardiac Echo and Ultrasound Ablation," Medical Imaging 2003: Ultrasonic and Signal Processing, vol. 5035, 2003, pp. 166-173.

Lafon et al., "Optmizing the Shape of Ultrasound Transducers for Interstitial Thermal Ablations," MEd Phys. Mar. 2002; 29(3): 290-7 (abstract only).

(56) References Cited

OTHER PUBLICATIONS

G. Ter Haar, "Ultrasound Focal Beam Surgery," Ultrasound in Med. & Biol., 1995, vol. 21, No. 9, pp. 1089-1100.

Seip et al., "Transurethral High Intensity Focused Ultrasound: Catheter Based Prototypes and Experimental Results," IEEE Ultrasonics Symposium Proceeding, 2000, 4 pages.

Toytman et al., "Tissue Dissection with Ultrafast Laser Using Extended and Multiple Foci," SPIE Proceeding, Optical Interactions with Tissues and Cells XXI, vol. 7562, 2010, 10 pages.

Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.

* cited by examiner

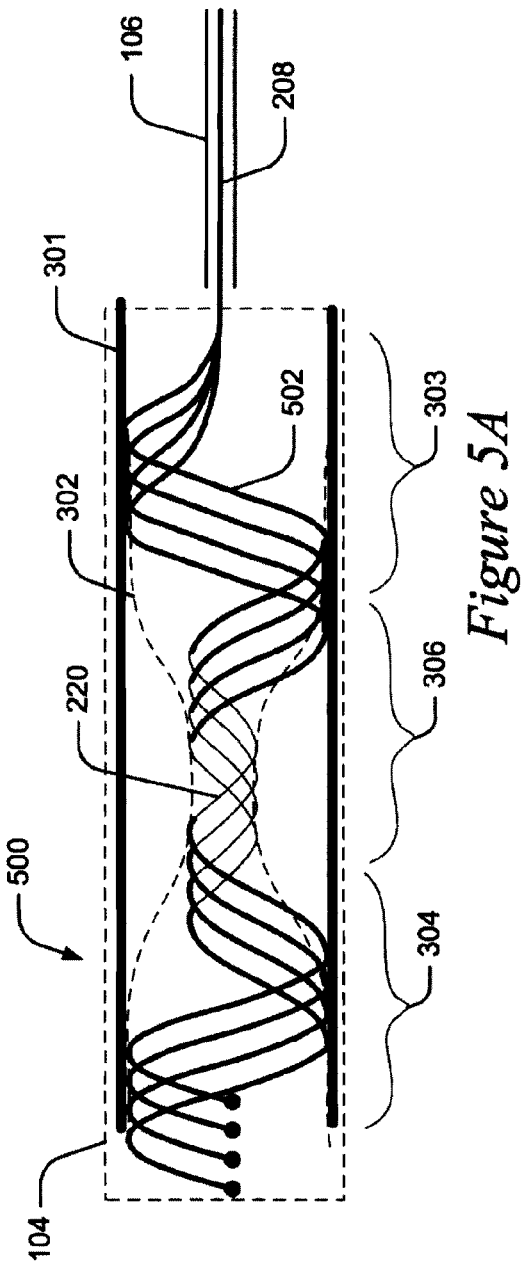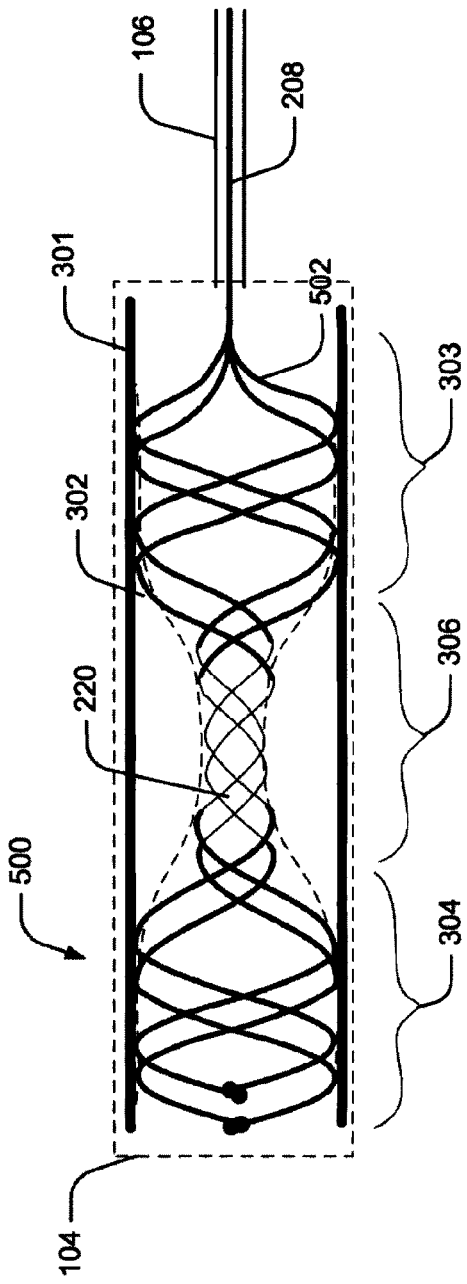
Figure 5A
Figure 5B

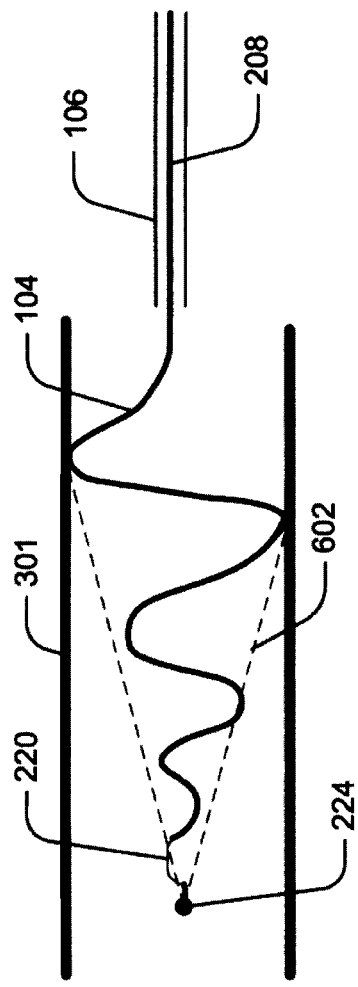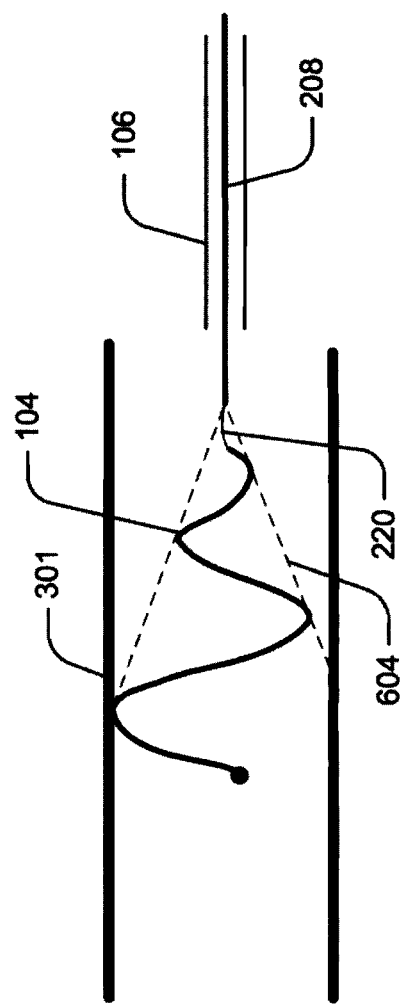

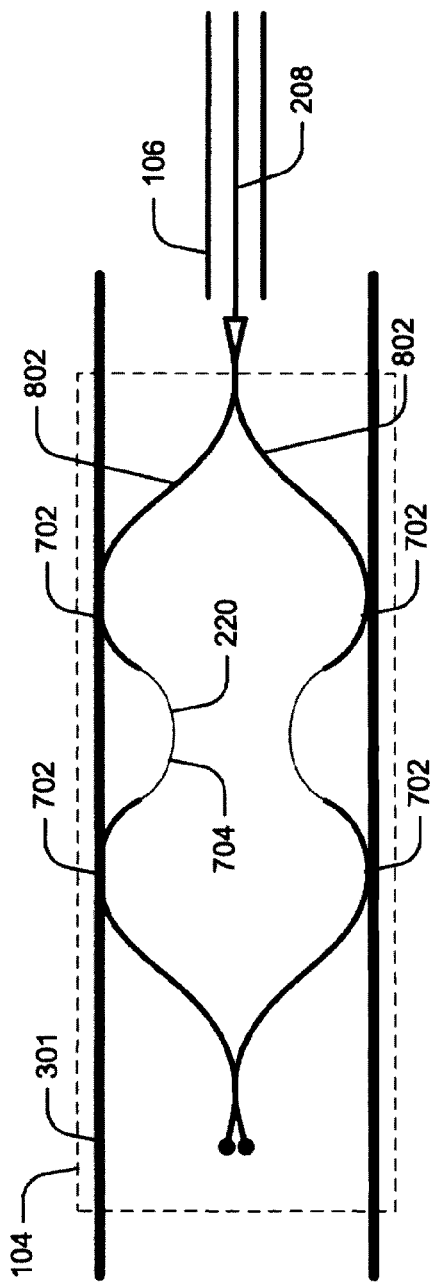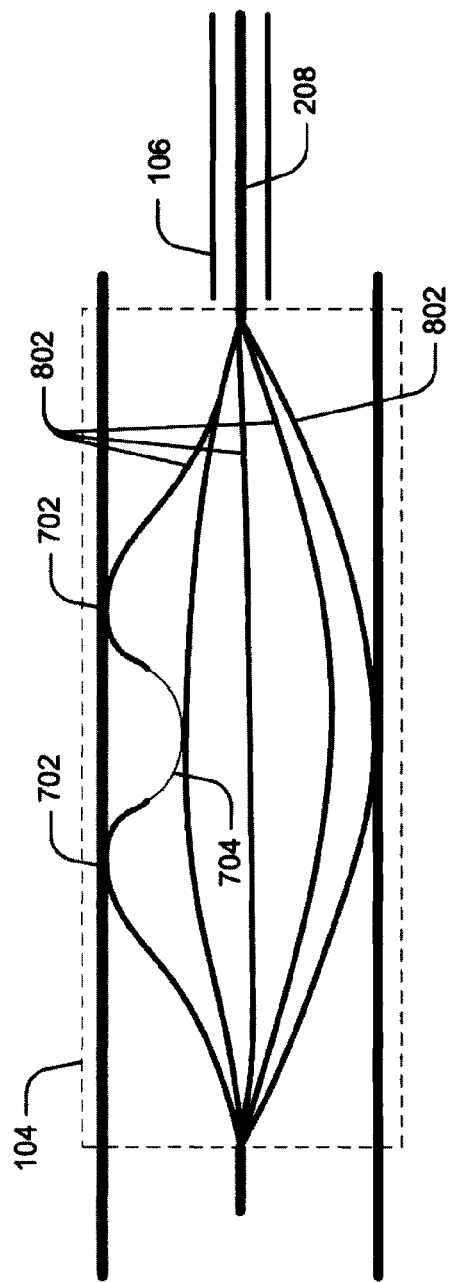

OFF-WALL ELECTRODE DEVICE AND METHODS FOR NERVE MODULATION

CROSS-REFERENCE TO RELATED APPLICATIONS

This application claims priority under 35 U.S.C. §119 to U.S. Provisional Application Ser. No. 61/581,430, filed Dec. 29, 2011, the entirety of which is incorporated herein by reference.

TECHNICAL FIELD

This disclosure relates to devices and methods for intravascular neuromodulation. More particularly, the technologies disclosed herein relate to apparatus, systems, and methods for achieving intravascular renal neuromodulation via thermal heating.

BACKGROUND

Certain treatments require temporary or permanent interruption or modification of select nerve functions. One example treatment is renal nerve ablation, which is sometimes used to treat conditions related to hypertension and congestive heart failure. The kidneys produce a sympathetic response to congestive heart failure, which among other effects, increases the undesired retention of water and/or sodium. Ablating some nerves running to the kidneys may reduce or eliminate this sympathetic function, providing a corresponding reduction in the associated undesired symptoms.

Many nerves, including renal nerves, run along the walls of or in close proximity to blood vessels, and these nerves can be accessed via the blood vessel walls. In some instances, it may be desirable to ablate perivascular renal nerves using a radio frequency (RF) electrode. Such treatment, however, may have an increased risk of thermal injury to the vessel at the electrode and other undesirable side effects such as, but not limited to, tissue damage, clotting, and/or protein fouling of the electrode. To prevent such undesirable side effects, some techniques attempt to increase the distance between the vessel walls and the electrode.

Therefore, there remains room for improvement and/or alternatives in providing systems and methods for intravascular nerve modulation.

SUMMARY

The disclosure is directed to several alternative designs, materials, and methods of manufacturing medical device structures and assemblies.

Accordingly, some embodiments pertain to an ablative catheter system for nerve modulation through the wall of a blood vessel, including a catheter sheath extending along a central elongate axis and having a proximal end, a distal end, and a lumen extending from the proximal to the distal end. The catheter system further includes an elongate member with a proximal end and a distal end, and an expandable ablative member coupled to the distal end of the elongate member. The ablative member may include an insulating section and a bare electrode section. Further, the ablative member is configured such that it may be moved between a collapsed position and an expanded position. In the expanded position, a portion of the insulative section contacts the walls of the vessel lumen and the bare electrode section is at a distance from the vessel lumen wall. The ablative member may be self-expanding or may be expanded by an actuating means such as a balloon or by push-pull actuation. Further, the ablative member may be one or more spiral coils formed as an hourglass. Alternatively, the ablative member may be formed of conductor wires expandable to form two or more humps and one or more troughs in between. The bare electrode sections may be positioned in the troughs and the insulative sections may be positioned in the humps.

Some embodiments pertain to a renal ablation system for nerve modulation through the wall of a blood vessel, including an elongate member extending along a central elongate axis. The elongate member has a proximal end and a distal end. The system further includes a self-expandable ablative member coupled to the distal end of the elongate member. The ablative member may have one or more conductor wires, which include one or more bare electrode sections. The electrode sections have a proximal and distal end and these electrode sections may be positioned at approximately at the center of the ablative member. The conductor wires may further include one or more insulative sections coupled to one or both of the proximal and the distal end of the bare electrode sections. The ablative member is configured to switch between a collapsed position and an expanded position, such that in the expanded position, the insulative portions contact the wall of the blood vessel and the bare electrode sections are positioned at a distance from the wall of the blood vessel.

Some embodiments also pertain to a method for ablating a nerve perivascularly through a vessel lumen. The method includes advancing a nerve modulation catheter such as an ablative catheter intravascularly proximate a desired location in a vessel lumen. In some embodiments, the ablative catheter includes a catheter sheath and an expandable ablative member having one or more bare electrode sections approximately at the center of the ablative coil and one or more insulative sections extending from the proximal end and distal end of the bare electrode sections. The method further deploys the expandable ablative coil in an expanded position in the vessel lumen such that portions of the insulative sections contact the walls of the vessel lumen and the bare electrode sections maintain a distance from the walls of the vessel lumen. Next, the bare electrode sections are activated to ablate at least a portion of the renal nerve without injuring the vessel walls.

The summary of some example embodiments in not intended to describe each disclosed embodiment or every implementation of the disclosure.

BRIEF DESCRIPTION OF THE DRAWINGS

The present disclosure may be more completely understood in consideration of the following detailed description of various embodiments in connection with the accompanying drawings, in which:

FIGS. 5A-5B illustrate a side view of various example multi-filament ablative members.

FIGS. 6A-6B illustrate a side view of various example configurations of the ablative member.

FIG. 8 illustrates a side view of an example two-wire ablative member in the expanded position.

FIG. 9 illustrates a side view of an example multi-wire ablative member in the expanded position.

Figure 1:
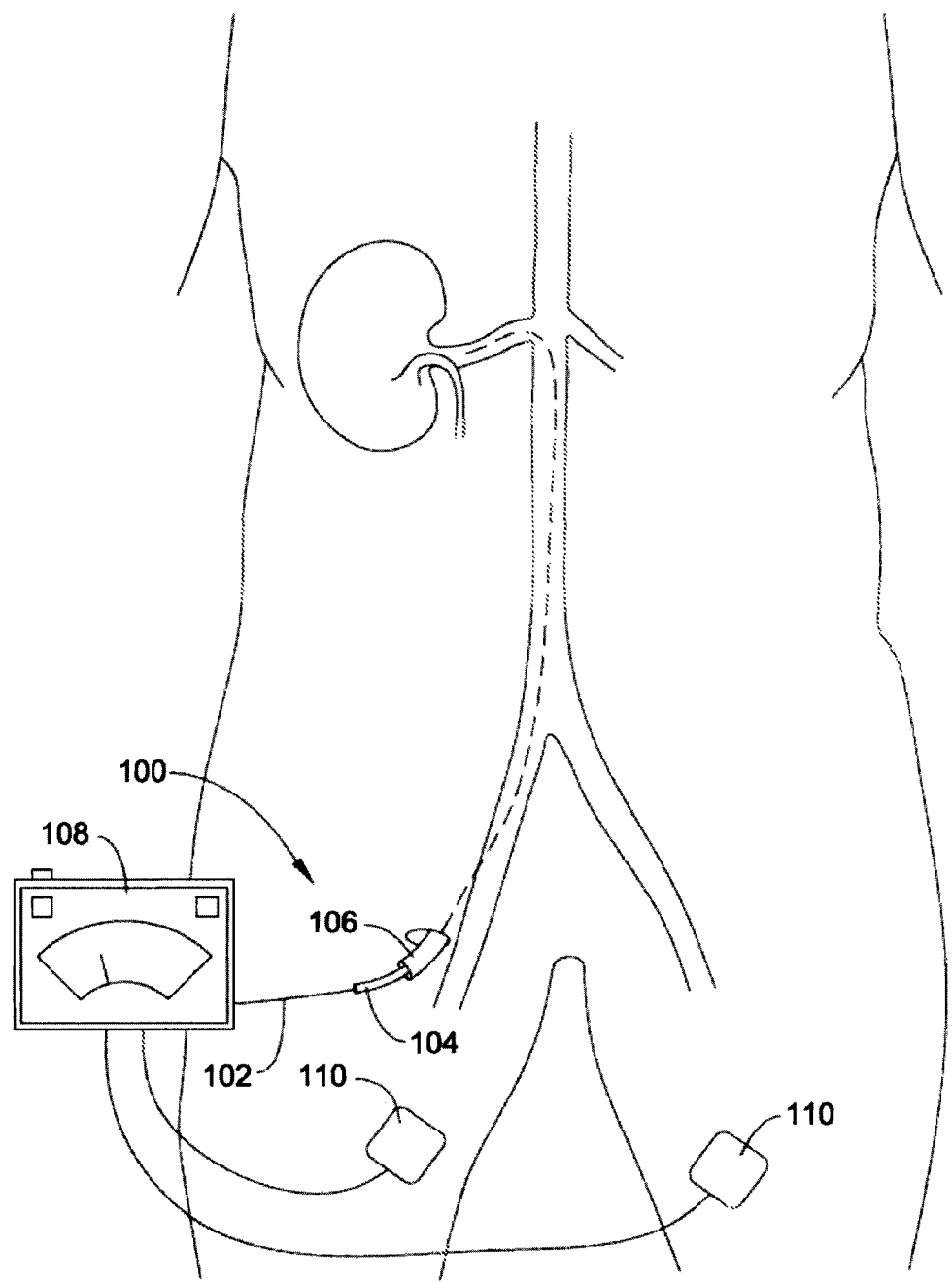
FIG. 1 is a schematic view illustrating a renal nerve modulation system in situ.

While embodiments of the present disclosure are amenable to various modifications and alternative forms, specifics thereof have been shown by way of example in the drawings and will be described in detail. It should be understood, however, that the intention is not to limit aspects of the disclosure to the particular embodiments described. One the contrary, the intention is to cover all modifications, equivalents, and alternatives falling within the spirit and scope of the present disclosure.

DETAILED DESCRIPTION

For the following defined terms, these definitions shall be applied, unless a different definition is given in the claims or elsewhere in the specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant Figure.

The recitation of numerical ranges by endpoints includes all numbers within that range (e.g., 1 to 5 includes 1, 1.5, 2, 2.75, 3, 3.80, 4, and 5).

Although some suitable dimension ranges and/or values pertaining to various components, features, and/or specifications are disclosed, one of skill in the art, incited by the present disclosure, would understand desired dimensions, ranges and/or values many deviate from those expressly disclosed.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

While the devices and methods described herein are discussed relative to renal nerve modulation, it is contemplated that the devices and methods may be used in other applications where nerve modulation and/or tissue ablation are desired. In addition to nerve modulation, the present apparatus and methods can be applied to modulation or ablation of other tissues in the body.

In some instances, it may be desirable to ablate perivascular renal nerves with deep target tissue heating. However, as energy passes from an electrode to the desired treatment region, the energy may heat the fluid (e.g. blood) and tissue as it passes. As more energy is used, higher temperatures in the desired treatment region may be achieved, but may result in some negative side effects, such as, but not limited to, thermal injury to the vessel wall, blood damage, clotting, and/or electrode fouling past the electrode and the vessel wall. Positioning the electrode away from the vessel wall may provide some degree of passive cooling by allowing blood to flow past the electrode.

FIG. 1 is a schematic view of an illustrative renal nerve modulation system 100 in situ. System 100 may include one or more conductors 102 for providing power to an ablative member 104 disposed within a catheter sheath or guide catheter 106, the details of which can be better seen in subsequent figures. A proximal end of the conductor 102 may be connected to a control and power element 108, which supplies the necessary electrical energy to activate the one or more electrodes (not shown) at or near a distal end of the ablative member 104. In some instances, return electrode patches 110 may be supplied at a convenient location on the patient's body to complete the circuit. The control and power element 108 may include monitoring elements to monitor parameters such as power, temperature, voltage, impedance, pulse size and/or shape and other suitable parameters as well as suitable controls for performing the desired procedure. In some instances, the power element 108 may control a radio frequency (RF) electrode. The electrode may be configured to operate at a frequency of approximately 460 kHz. It is contemplated that any desired frequency in the RF range may be used, for example, from 100-500 kHz. However, it is contemplated that different types of energy outside the RF spectrum may be used as desired, for example, but not limited to ultrasound, microwave, and laser.

Figure 2A:
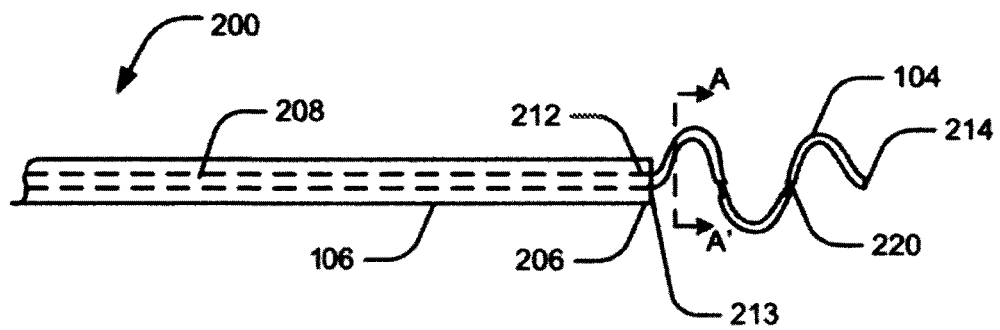
FIG. 2A is a schematic side view of the distal portion of an example ablative catheter system with an ablative member in the expanded state.
Figure 2B:
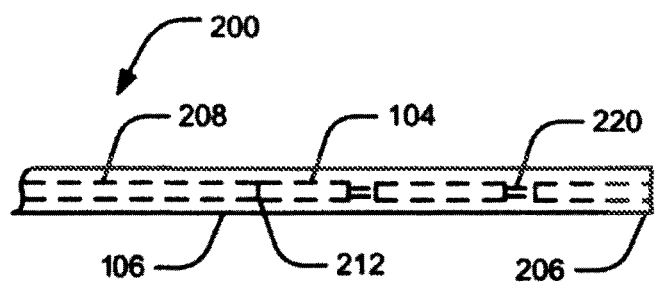
FIG. 2B illustrates the distal portion of the ablative member of FIG. 2A in a collapsed position.

FIGS. 2A and 2B are schematics of an exemplary ablative catheter system 200 according to embodiments of the present disclosure. More particularly, FIG. 2A is a side view of the catheter system 200 in an expanded state, while FIG. 2B is a side view of the catheter system 200 in a collapsed or compressed state. The ablative catheter system 200 includes catheter sheath 106 having a distal end 206, an elongate member 208 within the sheath lumen and having a distal end 212, and an expandable nerve modulation member, such as the ablative member 104 coupled to the elongate member's distal end 212. The ablative member 104 has a distal end 214. The catheter system 200 may further include proximal elements such as those shown in FIG. 1.

The sheath 106 may be substantially circular and it may be made of any suitable biocompatible material such as polyurethane, polyamide, polyether block amide (PEBA), silicones, fluoropolymer, PVC, metal or fiber reinforced material, a composite material, or a layered material, or a construction of multiple materials. Other suitable cross-sectional shapes such as elliptical, oval, polygonal, or irregular are also contemplated. Moreover, the sheath 106 may have a uniform flexibility along its entire length or adapted for variable flexure along portions of its length. For example, the sheath's distal end 206 may be more flexible while the remaining sheath may be less flexible. Flexibility allows the sheath 106 to maneuver turns in the circuitous vasculature, while greater stiffness provides the necessary columnar strength to urge the sheath 106 forward. The diameter of the sheath 106 may vary according to the desired application, but it is generally smaller than the typical diameter of a patient's vasculature. Moreover, the diameter of the sheath 106 may depend on the diameter of the elongate member 208 and the ablative member 104.

In one embodiment, the elongate member 208 is a conductor covered by an insulative material. The proximal end of the conductor may be connected to a power source such as an external power generator or battery incorporated in the handle. The distal end of the conductor may be connected to the ablative member 104 or other operative member.

FIG. 2A illustrates the ablative member 104 in an expanded state. In this state, some portions of the ablative member 104 contact the blood vessel walls and some portions remain at a distance from the walls. Electrodes 220 are positioned on the portions of the member 104 that remain at a distance from the wall. Depending on the desired application, electrodes 220 may be placed at various locations along the ablative member 104. For example, in one instance (not shown), the electrodes 220 may be placed slightly away from the wall. Alternatively, as shown in FIG. 2A, the electrodes 220 may be placed such that they are centered in the vessel.

Figure 2C:
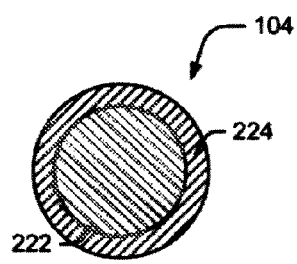
FIG. 2C is a cut away sectional view of the ablative member of FIG. 2A taken along line A-A'.

Moreover, the ablative member 104 may be formed of a conductor 222 with an insulative layer 224. FIG. 2C is a sectional view of the ablative member 104 taken along line A-A' in FIG. 2A, showing the conductor 222 and the layer 224. Portions of the ablative member 104 that contact the vessel surfaces include the layer 224, and portions where electrodes 220 are present are bare. For example, the center portion of the ablative member 104 may be without a layer 224, while all other portions may have the insulative layer 224. When electrical signals are passed through the conductor 222, the bare portions act as electrodes 220. Therefore, based on the required number and position of electrodes 220, portions of the ablative member 104 are left bare.

FIG. 2B is a schematic illustrating the distal portion of the ablative catheter system 100 with the ablative member 104 in the compressed state. From this state, the ablative member may be expanded using various actuating means, depending on the properties of the ablative member. For instance, the ablative member 104 may be self-expandable or expanded by application of a force. Self-expandable members may be formed of any material that can expand to its expanded configuration when released from a sheath. Such members may be formed of elastic materials such as stainless steel, shape memory alloys such as Nitinol or any other suitable material commonly known in the art.

According to another technique, pull wires (not shown) may be utilized. Pull wires may be attached to the member's distal end 214, for example. When the pull wire is pulled proximally, it places a tensile force on the ablative member 104, compressing it longitudinally to its radially expanded state. When the pull wire is released, the tensile force is released permitting the ablative member 104 to elongate to its radially collapsed state.

In case of ablative members 104 that are expanded by some external force, the member 104 does not expand on its own and an expansion means may be required to place an outward radial force on the member 104 to expand it. Such expansion means (not shown) may include balloons or dilators. Other such expansion means may also be utilized without departing from the scope of the present disclosure. For example, means such as springs, or levers may be utilized to expand the ablative member 104. Similarly, the ablative member 104, itself, may be formed of pivotal structures connected to one another. For instance, the member may be formed of multiple wires connected to one another along pivotal joints. An outward force on the pivotal point expands the various wires connected to the point, expanding the ablative member 104.

The expansion of the ablative member should be such that it does not cause damage to the artery by exerting a large force on the vessel walls. To prevent such large expansion force, the ablative member may include visualization devices such as cameras, fluorescent dyes, radiopaque markers or other visualization aids to visualize the extent of expansion. Further, the ablative member may include a force or expansion-limiting component that prevents the member from expanding beyond a certain limit. Often, the expansion limit may be set during manufacturing of the ablative member. For example, operators may know the average size of renal arteries, and they may ensure the ablative member does not expand beyond the average artery size. For example, the diameter of the expanded member may be maintained below about 4 mm, 6 mm, 8 mm or other desired size.

FIGS. 2A-2C illustrate a general ablative catheter system and ablative member 104 according to embodiments of the present disclosure. The following Figures and description illustrate specific exemplary configurations of the ablative member 104.

Figure 3:
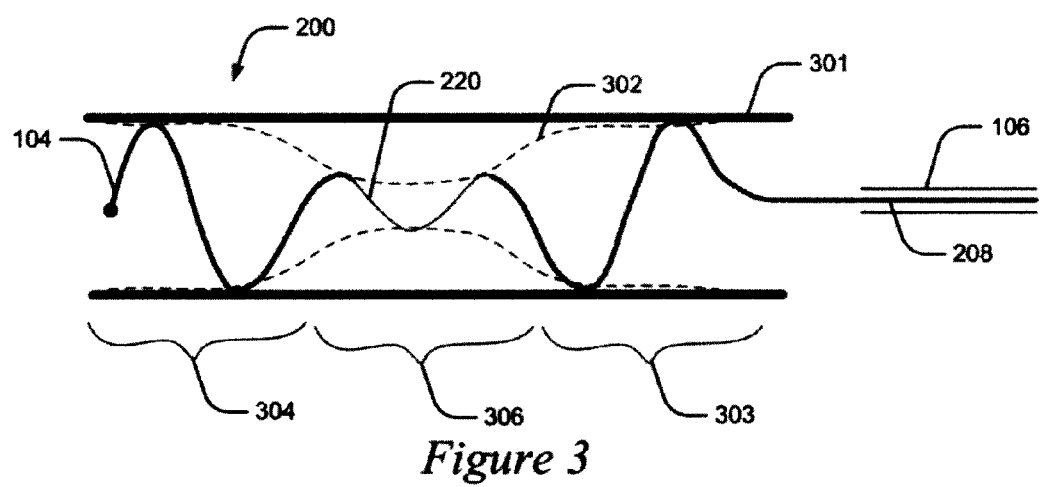
FIG. 3 illustrates a side view of the distal end of an example ablative catheter system in an expanded position within a blood vessel.

FIG. 3 is a schematic illustrating a distal portion of the ablative catheter system 200 within a blood vessel 301 in a patient's body. Here, the ablative member 104 is in the expanded state. The ablation member spirals into a helical, hourglass shape, generally indicated as hourglass shape 302. Further, the ablative member 104 may be formed as a spiral electrode coil having a proximal portion 303, a distal portion 304, and a central portion 306. The proximal and distal portions are covered with an insulative material, and a portion of the central portion 306 is bare, forming electrode 220.

As illustrated, the distal and proximal portions expand the most, deviating to such a degree from the centre of the vessel that they contact the wall of the blood vessel. The central portion 306, on the other hand, expands less (or not all all), deviating from the central longitudinal axis such that a gap is formed between the wall of the blood vessel 301 and the electrode 220.

The hourglass shape 302 is formed with the proximal and distal ends forming the two glasses and the central portion 306 forming the stem between the glasses. This shape, eliminates the chance of the electrode 220 touching the artery walls and causing wall injury. Further, being centered in the artery, the electrode 220 may circumferentially radiate RF energy equally ablating the nerves surrounding the artery.

The curvature of the central portion 306 may be controlled by the heat set geometry of the coil. For example, a small amount of narrowing may be used to position the electrode 220 about 0.5 mm from the artery wall. Alternatively, more narrowing may be incorporated to position the wire close to the center of the artery. In some embodiments, the electrode 220 may be arranged at any place along the spiral except the portions contacting the wall of the blood vessel 301. For example, to ablate nerve tissues closer to one side of the vessel wall, the electrode 220 may be placed anywhere between the central portion 306 and the proximal or distal portions.

The rigidity and characteristics of the material used to form the ablative member 104 determine the member's expandability. For example, the thickness of the material may vary between the central portion 306, and the distal and proximal portions, causing the central portion 306 to deviate slightly and the proximal and distal portions to deviate more. Similarly, the material composition may vary between the central and end portions varying the expandability of these portions. For example, materials such as, but not limited to, stainless steel or nitinol may be used to form one portion, while tungsten, platinum, palladium, other metals or a suitable polymer may be used to form other portions. Other techniques to vary the expandability of the coil may be employed just as easily such as varying the heat treatment of the thermal "set" of the material along the length, varying the material dimensions, varying coatings or coverings, etc.

Figure 4:
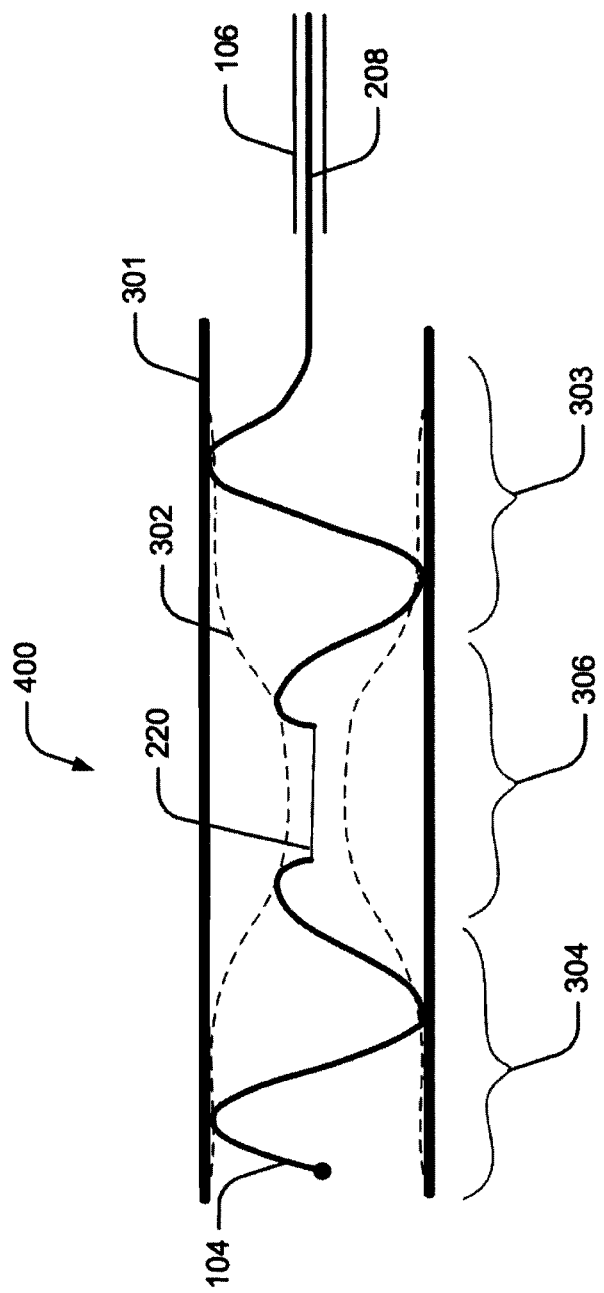
FIG. 4 illustrates another side view of an example ablative catheter system according to some embodiments of the present disclosure.

FIG. 4 illustrates the distal portion of an exemplary ablative catheter system 400 in the blood vessel 301. This example is similar to FIG. 3 except the central portion 306 is straightened such that the electrode 220 is arranged to be a straight segment along the center of the artery. This configuration, thus, applies equal circumferential RF ablation along the length of electrode 220.

FIGS. 5A and 5B illustrate the distal portion of another exemplary ablative catheter system 500. Here, the ablative member 104 includes multiple self-expandable coils or filaments 502. The coils may all expand in the same direction as illustrated in FIG. 5A, or expand in different directions, as illustrated in FIG. 5B. Each coil may independently form an hourglass configuration or the complete multi-filament structure may also form the hourglass configuration. Further, the coils may be loosely braided with the bare electrode portions of each coil in the central portion 306.

Alternatively, the bare electrode portion for each coil may be at a different location along the coil, so that the electrodes 220 target different ablation sites. For example, the electrode 220 for one coil may be in the central portion 306, for another coil may be in the proximal portion 303, and for a third coil may be in the distal portion 304. Further, the degree of expansion, the materials used, and the thickness of the coils may vary within the coils without departing from the scope of the present disclosure. Moreover, different levels of narrowing may be carried out for the different coils so that the electrodes 220 are at a varied distance from the artery walls.

Using multiple filaments 502, more electrodes 220, or electrodes having larger surface area, may be created in the central portion 306, which can together deliver more energy than a single electrode 220 without blood coagulation or electrode fouling, and therefore ablate a given nerve more quickly and efficiently. Increased energy delivery, however, may raise the temperature around the coil considerably and, therefore, blood with greater velocity may be required to cool the area sufficiently. A number of cooling techniques are known in the art and any of these cooling techniques may be utilized to cool the vessel without departing from the scope of the present disclosure.

The multi-strand braid of FIG. 5 may be formed of metal, polymer, or a combination of the two. For example, the polymer filaments may provide centering and position control, while the metal may be used as the electrode 220. In one embodiment, the filaments 502 may have a metal core and a polymer outer covering over the insulative portions. Further, any suitable biocompatible metal or polymer may be utilized to form the filaments 502. Exemplary metals may include, but not limited to, platinum, gold, stainless steel, steel, cobalt alloys, nitinol, or other such non-oxidizing materials. In some instances, titanium, tantalum, or tungsten may be used. Exemplary polymers include polyurethane, polyamide, polyether block amide (PEBA), silicones, fluoropolymer, PVC, a composite material, a layered material, or a construction of multiple materials.

The embodiments illustrated in FIGS. 2-5 illustrate a self-expandable member formed into an hourglass shaped coil. FIGS. 6A and 6B illustrate a few alternate embodiments where the coil may take different shapes. For example, FIG. 6A illustrates an ablative member 104 in the form of a decreasing spiral 602. The proximal end of the member 104 may expand the most, contacting the wall of the blood vessel 301, and the distal end of the member 104 may not expand at all. The ablative member 104 thus forms an inverted V shaped member. The electrode 220 may be placed at the distal end of the member 104, or at any other positions along the coil that do not contact the walls of the artery. In case the electrode 220 is placed at the distal end, it may be placed at a little distance from the distal end of the member 104. This insulative portion 224 at the distal tip ensures that even if the distal end contacts the vessel walls inadvertently, the electrode does not contact the wall.

FIG. 6B illustrates the ablative member in the form of an increasing spiral 604 where the proximal end of the ablative member 104 expands the least and the distal end expands the most. Here, the distal end contacts the vessel walls, while the central and proximal portions do not. Electrodes 220 may be placed anywhere along the central or proximal portions of the ablative member 104 without departing from the scope of the present disclosure. Further, two or more electrode 220 may also be placed at different locations along the ablative member 104 to ablate different nerve sites without moving the catheter system 200.

It will be understood that other variations in configuration are possible as long as the ablative member 104 includes insulative portions in contact with the vessel walls and bare electrode portions away from the vessel walls. For example, the ablative member 104 may be made of expandable conductor wires shaped as an ellipse or a circle. The elliptical or circular member may be stored in a compressed state within the sheath 106, and when the member 104 is actuated to extend beyond the distal end 206 of the sheath 106, the member 104 may expand. In this type of member 104, the electrodes 220 may be positioned at the distalmost or proximal end of the member 104. Alternatively, the ablative member 104 may have a zigzag shape, bends, or bumps to position the electrodes 220 as desired.

Figure 7A:
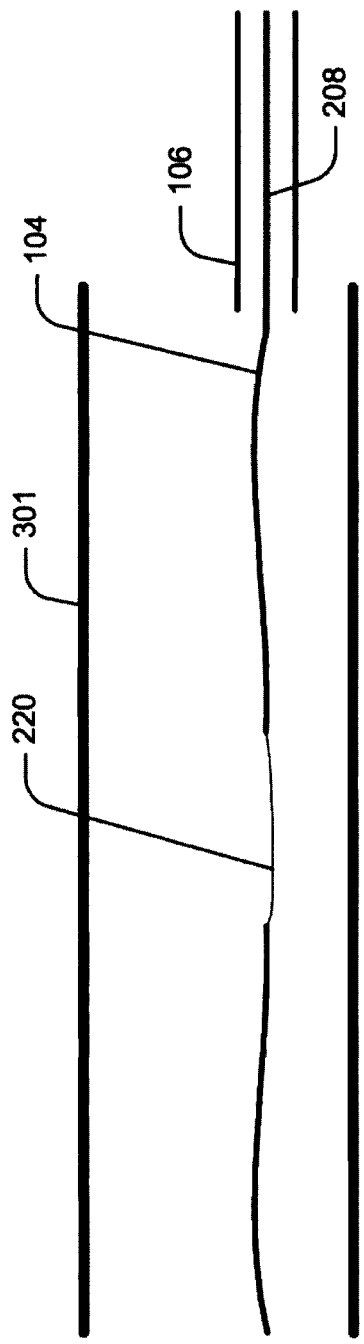
FIG. 7A illustrates another side view of an example embodiment of the ablative member in a compressed state.
Figure 7B:
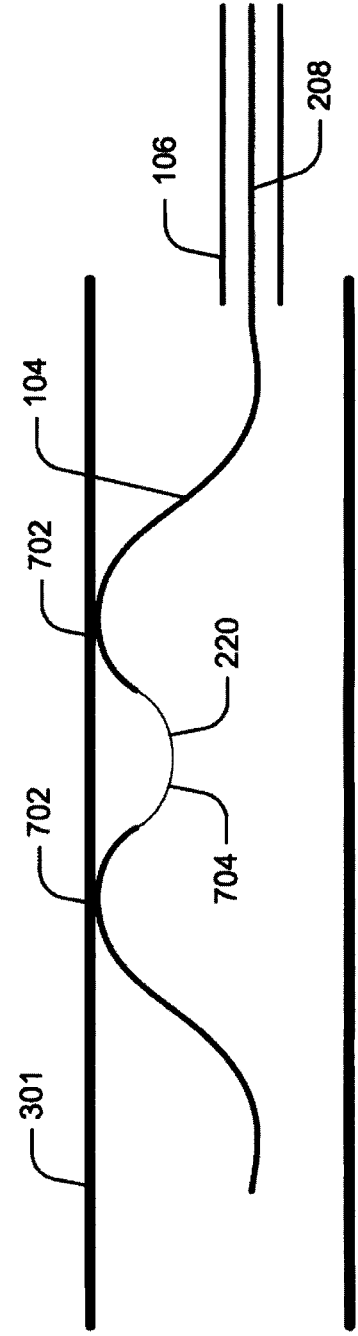
FIG. 7B illustrates the ablative member of FIG. 7A in an expanded position.

FIGS. 7A and 7B illustrate yet another exemplary ablative member 104. More particularly, FIG. 7A illustrates the ablative member 104 in the compressed state and FIG. 7B illustrates the ablative member 104 in the expanded or deployed state. In the compressed state, the ablative member 104 remains straight within the blood vessel 301. In case the ablative member 104 is self-expandable, any known technique may be utilized to keep the ablative member 104 compressed, such as by compression within the sheath 106 or by using pull wires. In case the ablative member 104 requires external force, the external force is not applied in the compressed state.

In case of ablative member 104, for expansion, the member 104 may be extended beyond the sheath 106, or the pull wires may be released. Alternatively, external forces, such as a balloon, a dilator, or other such means may be utilized to expand the member 104. In the expanded state, the proximal and distal portions of ablative member 104 remain along the longitudinal axis while a central portion expands to form two humps 702. A trough 704 is formed between the two humps 702 and this trough 704 is the bare portion of the ablative member forming the electrode 220.

As described previously, the degree of expandability of the humps 702 and their degree of inclination may depend on a number of factors such as material used, thickness of the material, desired geometry, etc. For example, the bare electrode portion may be narrowed such that it dips away from the artery walls. In other embodiments, the wire may have three or more humps 702, allowing for the placement of multiple electrodes 220 on the same wire. Moreover, the distance of the trough 704 from the peak of the humps 702 may vary allowing operators to place electrodes 220 at different distances from the artery walls, and therefore adjusting the distribution of RF energy.

FIG. 8 illustrates another exemplary ablative member, which includes two electrode wires 802 expanding in opposite directions, and therefore centering the ablative member 104 with respect to the vessel 301. It will be understood that, instead of both the wires 802 having the same expandable configuration (as shown in FIG. 8), their configurations may vary. For example, one wire may include two humps 702 and the other wire may include three or no humps. No humps may be formed when the wire forms a simple bow structure. These wires 802 may be completely insulated and they may not include any electrodes.

It will be understood that, instead of two wires 802, multiple such electrode wires 802 may be incorporated in the ablative member 104. FIG. 9 illustrates such an embodiment. In some instances, each wire 802 may include at least one portion contacting the blood vessel wall, and at least some wires 802 may include a bare electrode region. As illustrated in this Figure, only one wire includes an electrode 220, while the other wires 802 are merely included for centering and positioning the ablative member 104. In some instances, the bare electrode region of all the wires may be equidistant from the vessel walls. Alternatively, the electrodes 220 may be placed at different distances from the wall of the blood vessel 301. Some electrodes 220 may be closer to the artery walls than others. Moreover, the electrodes 220 may not be placed in the trough 704 between the humps 702. Instead, they may be placed on any other portions of the wires 802 not contacting the vessel surface. For example, the electrodes 220 may be placed towards the distal or proximal ends of the ablative member 104.

The ablative members 104 illustrated in FIGS. 2-9 have a configuration that allows blood to flow through the expandable material for cooling the structure and the artery wall. Even the multi-filament structures are loosely braided structures that allow blood to flow through the member 104, cooling it. Because the structure does not block much of the artery during modulation, this structure minimizes blood stasis, reduces thrombosis, and provides renal perfusion.

Further, to monitor the temperature of the electrodes 220 and the blood vessel 301 walls, one or more sensors, such as temperature sensors, may be placed at different portions of the ablative member 104. For instance, one sensor may be placed near the electrode 220 to monitor electrode fouling or electrode temperature and another sensor may be placed in the portion contacting the vessel wall to measure the temperature at the blood vessel. External devices connected to the sensors may be configured to raise alerts if any of the sensors detect temperatures over a preconfigured threshold value. If an alert is raised, operators may discontinue modulation until the temperature at the electrode or at the vessel wall returns under the threshold value. Alternatively, operators may simply monitor the temperatures and discontinue when they feel temperatures exceed a certain value.

The insulative covering on the ablative member 104 provide electrical isolation but still may conduct heat. This heat conductive property allows operators to place temperature sensors such as thermocouples on the insulative portions to measure temperature.

The ablative catheter system 200 may be operated in various modes. In unipolar ablation, a distant ground pad or electrode is typically used to complete the circuit. In one embodiment, the system 200 may be operated in a sequential unipolar ablation mode. In this mode, the electrodes may each be connected to an independent power supply such that each electrode may be operated separately. In sequential unipolar ablation, one electrode may be activated at a time. The next electrode is activated only after a first electrode is activated and deactivated.

In another instance, the system 200 may operate in a simultaneous unipolar mode. In this mode, the electrodes may be activated simultaneously. In some embodiments, the electrodes may each be connected to independent electrical supplies. Independent power supplies provide more control of the ablation energy supplied to each electrode. Alternatively, the electrodes may all be connected in parallel to the same electric supply. In this mode, more current may be dispersed radially as all the electrodes collectively emanate current at the same time. This dispersion may result in a more effective, deeper penetration compared to the sequential unipolar mode.

In another embodiment, a bipolar ablation mode may also be employed. In this mode, two electrodes disposed at the treatment location may be used to complete the circuit without a distant ground pad or electrode such that current may flow around the ablative member from one electrode to the other. In general, either sequential or simultaneous unipolar mode may penetrate more deeply than the bipolar mode. Any of the embodiments described in this disclosure may be operated in any of the above-described modes.

In use, the system 200 may be introduced percutaneously as is conventional in the intravascular medicinal device arts. For example, a guidewire may be introduced percutaneously through a femoral artery and navigated to a renal artery using standard radiographic techniques. The catheter sheath 106 may be introduced over the guide wire and the guide wire may be withdrawn. The elongate member and the ablative member may then be introduced in the catheter sheath 106 and urged distally to the desired location. Once there, the sheath may be retracted proximally to allow the ablative member to expand or the ablative member may be urged distally to extend beyond the distal end of the sheath.

The electrodes may then be activated to ablate nerve tissue. During this procedure, the ablative member may continuously monitor the temperature at the electrodes and the vessel walls. Further, the electrodes may be activated sequentially or simultaneously, as desired. Known monitoring techniques may be utilized to monitor the tissue being ablated. Once the tissue is sufficiently ablated, the catheter sheath may be advanced or the ablative member may be retracted to compress the ablative member and retrieve it from the patient's body.

Those skilled in the art will recognize that the present disclosure may be manifested in a variety of forms other than the specific embodiments described and contemplated herein. Accordingly, departure in form a and detail may be made without departing from the scope and spirit of the present disclosure as described in the appended claims.

What is claimed is:

1. An ablative catheter for nerve modulation through a wall of a blood vessel, the catheter comprising:

a catheter sheath having a proximal end, a distal end, and a lumen extending from the proximal to the distal end;

an elongate member extending along a central elongate axis within the lumen of the catheter sheath, the elongate member having a proximal end and a distal end;

an expandable ablative member coupled to the distal end of the elongate member having one or more insulative sections connected to a bare electrode section;

wherein the ablative member is configured to switch between a collapsed position and an expanded position extending out of the distal end of the catheter sheath such that a portion of the insulative section contacts the wall of the blood vessel and the bare electrode section is disposed at a distance from the wall of the blood vessel, the expandable ablative member having a generally helical shape of variable outer diameter; and wherein the ablative member is an expandable wire configured to form two or more humps and one or more troughs in between the two or more humps in the expanded position such that the insulative sections form the two or more humps and the bare electrode section forms the one or more troughs.

2. The ablative catheter of claim 1, wherein the ablative member is self-expandable.

3. The ablative catheter of claim 1, wherein the ablative member is expanded by an actuating means.

4. The ablative catheter of claim 1, wherein the ablative member is a spiral coil configured in an hourglass shape having a first end, a second end and a waist therebetween.

5. The ablative catheter of claim 4, wherein the insulative sections form the two ends of the hourglass shape and the bare electrode section forms a waist of the hourglass shape.

6. The ablative catheter of claim 4, wherein the ablative member includes a plurality of spiral coils loosely braided.

7. The ablative catheter of claim 1, wherein the ablative member includes a plurality of expandable wires.

8. The ablative catheter of claim 1, wherein, in the expanded position, an outer diameter of the ablative member increases distally.

9. The ablative catheter of claim 1, further comprising one or more temperature sensors coupled to the portion of the insulative section in contact with the wall of the blood vessel in the expanded position.

10. A renal ablation system for nerve modulation through a wall of a blood vessel, the system comprising:
    an elongate member extending along a central elongate axis, the elongate member having a proximal end and a distal end;
    an expandable ablative member coupled to the distal end of the elongate member, the ablative member having one or more conductor wires, the conductor wires comprising:
        one or more bare electrode sections each having a proximal end and a distal end, and
        one or more insulative sections;
    the ablative member configured to switch between a collapsed position an expanded position;
    wherein in the expanded position, the insulative portions contact the wall of the blood vessel and the bare electrode sections are positioned at a distance from the wall of the blood vessel; and
    wherein, in the expanded position, one or more of the conductor wires are configured to form two or more humps and one or more troughs, such that the insulative sections form the two or more humps and the bare electrode sections form the one or more troughs.

11. The renal ablation system of claim 10, wherein the conductor wires are spiral coils.

12. The renal ablation system of claim 11, wherein, in the expanded position, the spiral coils forms an hourglass shape.

13. The renal ablation system of claim 11, wherein the ablative member includes multiple spiral coils loosely braided to form an hourglass shape.

14. The renal ablation system of claim 10, wherein the expandable ablative member is biased to the expanded position.

15. The renal ablation system of claim 10, wherein the expandable ablative member includes at least one insulative section proximal the bare electrode sections and at least one insulative section distal the bare electrode sections.

16. A method for ablating tissue through a vessel lumen, the method comprising:
    advancing an ablative catheter intravascularly proximate a desired location in a blood vessel, the ablative catheter including an elongate member and an expandable ablative member having one or more bare electrode sections disposed along a center region of the ablative member and one or more insulative sections extending from the proximal end and distal end of the bare electrode sections;
    wherein the ablative member is an expandable wire configured to form two or more humps and one or more troughs in between the two or more humps in the expanded position such that the insulative sections form the two or more humps and the bare electrode sections form the one or more troughs;
    deploying the expandable ablative member in an expanded position in the vessel lumen such that portions of the insulative sections contact a wall of the blood vessel and the bare electrode sections maintain a distance from the wall of the blood vessel; and
    activating the bare electrode sections to ablate at least a portion of a target tissue.

17. The method of claim 16, wherein the target tissue is perivascular nerve tissue.

18. The method of claim 16, wherein the expandable ablative member includes a plurality of generally helical elongate members, each of the plurality of generally helical elongate members comprising a bare electrode section and an insulative section.

* * * * *